United States Patent
Uflacker et al.

(10) Patent No.: US 6,261,257 B1
(45) Date of Patent: *Jul. 17, 2001

(54) DIALYSIS GRAFT SYSTEM WITH SELF-SEALING ACCESS PORTS

(76) Inventors: Renan P. Uflacker; Andre B. Uflacker, both of 548 Overseer's Retreat, Mt. Pleasant, SC (US) 29464

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/317,232

(22) Filed: May 24, 1999

Related U.S. Application Data

(60) Provisional application No. 60/086,777, filed on May 26, 1998.

(51) Int. Cl.[7] ............................. A61M 5/32; A61M 5/00; A61F 2/06

(52) U.S. Cl. ............................ 604/9; 604/175; 623/1.1

(58) Field of Search ........................ 623/1, 12, 1.1; 604/8, 9, 175, 6.14, 6.09, 6.19

(56) References Cited

U.S. PATENT DOCUMENTS

| | | | |
|---|---|---|---|
| 3,826,257 | * 7/1974 | Buselmeier | 128/214 |
| 4,405,319 | 9/1983 | Cosentino | 604/175 |
| 4,421,507 | 12/1983 | Bokros | 604/52 |
| 4,496,350 | * 1/1985 | Cosentino | 604/175 |
| 4,512,761 | * 4/1985 | Raible | 604/8 |
| 4,559,039 | 12/1985 | Ash et al. | 604/175 |
| 4,639,247 | 1/1987 | Bokros | 604/175 |
| 4,822,341 | * 4/1989 | Colone | 604/175 |
| 4,897,081 | 1/1990 | Poirier et al. | 604/175 |
| 4,898,669 | 2/1990 | Tesio | 210/232 |
| 4,936,826 | 6/1990 | Amarasinghe | 604/52 |
| 5,041,098 | 8/1991 | Loiterman et al. | 604/175 |
| 5,192,310 | * 3/1993 | Herweck et al. | 623/1 |
| 5,421,814 | 6/1995 | Geary | 604/4 |
| 5,443,497 | 8/1995 | Venbrux | 623/1 |
| 5,520,632 | * 5/1996 | Leveen et al. | 604/9 |
| 5,647,855 | 7/1997 | Trooskin | 604/175 |
| 5,704,915 | 1/1998 | Melsky et al. | 604/175 |
| 5,728,103 | 3/1998 | Picha et al. | 606/108 |
| 5,807,356 | 9/1998 | Finch, Jr. et al. | 604/284 |
| 5,849,036 | 12/1998 | Zarate | 623/1 |
| 5,876,366 | 3/1999 | Dykstra et al. | 604/4 |
| 5,879,320 | 3/1999 | Cazenave | 604/8 |

OTHER PUBLICATIONS

Munda et al., "Polytetrafluoroethylene Graft Survival in Hemodialysis," JAMA, Jan. 14, 1983, vol. 249, No. 2, pp. 219–222.

Anderson et al., "One Hundred Polytetrafluroethylene Vascular Access Grafts," Dialysis & Transplantation, Mar. 1980, vol. 9, No. 3, pp. 237–238.

Palder, et al., "Vascular Access for Hemodialysis," Ann. Surg., Aug. 1991, vol. 202, No. 2, pp. 235–239.

Levowitz et al., "Prosthetic Arteriovenous Fistula for Vascular Access in Hemodialysis," The American Journal of Surgery, Sep. 1976, vol. 132, pp. 368–372.

Raju, "PTFE Grafts for Hemodialysis Access," Ann. Surg. Nov. 1987, vol. 206, No. 5, pp. 666–673.

Volder et al., "A–V Shunts Created in New Ways," Trans. Amer. Soc. Artif. Int. Organs, 1973, vol. XIX, pp. 38–42.

(List continued on next page.)

*Primary Examiner*—Corrine McDermott
*Assistant Examiner*—Hieu Phan
(74) *Attorney, Agent, or Firm*—Hodgson Russ LLP

(57) ABSTRACT

This invention provides a dialysis-access graft fistula having self-sealing ports for use in hemodialysis. The self-sealing ports can be repeatedly used for the cannulation required for the blood flows associated with hemodialysis. The ports self-seal after each puncture.

22 Claims, 3 Drawing Sheets-

OTHER PUBLICATIONS

Kaplan et al., "Comparison of 'PTFE' and Bovine Grafts for Blood Access in Dialysis Patients," Trans. Amer. Soc. Artif. Int. Organs, 1976, vol. XXII, pp. 388–393.

Rizzuti et al., "Extended Patency of Expanded Polytetrafluoroethylene Grafts for Vascular Access Using Optimal Configuration and Revisions," Surgery, Gynecology & Obstetrics, Jan. 1988, vol. 166, pp. 23–27.

Baker et al., "Expanded Polytetrafluoroethylene (PTFE) Subcutaneous Arteriovenous Conduit: An Improved Vascular Access for Chronic Hemodialysis," Trans. Amer. Soc. Artif. Int. Organs, 1976, vol. XXII, pp. 382–387.

Flores et al., "Dacron Arterio–Venous Shunts for Vascular Access in Hemodialysis, "Trans. Amer. Soc. Artif. Int. Organs, 1973, vol. XIX, pp. 33–37.

* cited by examiner

DIALYSIS GRAFT SYSTEM WITH SELF-SEALING ACCESS PORTS

CROSS-REFERENCE TO RELATED APPLICATION

Applicant hereby claims priority based on Provisional Application No. 60/086,777 filed May 26, 1998, and entitled "Dialysis Graft With Self-Sealing Ports" which is incorporated herein by reference.

FIELD OF INVENTION

The present invention relates generally to the field of dialysis grafts, and more specifically to a dialysis graft having self-sealing ports for repeated cannulation.

BACKGROUND OF THE INVENTION

Hemodialysis is now a commonly practiced method of treating patients suffering from renal failure. Hemodialysis machines serve to remove life-threatening chemicals from the blood stream, when the kidneys can no longer effectively remove such chemicals.

In order to perform hemodialysis, access must be obtained to the blood flow system, and blood flows of 150 to 400 ml/minute are required. Blood from veins is inadequate to meet these flow requirements, and repeated puncture of a large artery is not feasible.

Accordingly, a medical procedure has been developed whereby a fistula is created by surgically anastamosing a superficial artery and a nearby vein. The fistula is a surgical connection of an artery to a vein. When such a connection is created, the blood flow through the blood vessels involved is increased since the flow resistant capillaries are bypassed. The pressure at the venous side of the fistula is also increased, causing the vein to enlarge its diameter and causing the walls of the vein to thicken. Once these changes have taken place, the transformed vein becomes a site with a suitably large diameter and blood flow to puncture with needles for the purpose of connecting the patient to a dialysis machine.

If a native vein is not available for the anastomosis because the patient's blood vessels are not suitable for the formation of a fistula or the patient's blood vessels are not healthy enough for a fistula to be created, an artificial vessel or vascular graft is used to bridge an artery and a nearby vein. The material of the graft is suitable for puncturing with needles to achieve the necessary access to the patient's blood system.

These type of grafts are often connected between the distal radial artery and the cephalic or basilic vein. Each end of the fistula is anastomosed in an end-to-side fashion to the respective artery or vein. The most commonly used material to form prosthetic vascular grafts is expanded polytetrafluoroethylene (PTFE). And cannulation of arteriovenous fistulas or graft fistulas with 14–16 gauge needles permits blood flow sufficient to carry out hemodialysis.

The grafts are implanted entirely below the skin to reduce the risk of infection and to provide better comfort to the patient between dialysis treatments. A hypodermic needle is used to cannulate the vessel through the skin. During cannulation of the graft fistulas, direct punctures of the graft walls are made with the needles. One puncture is made in the graft wall in the arterial side and one puncture is made in the venous side. Repeated punctures of the graft material promote rupture of the graft, pseudoaneurysms, and the development of organized thrombus within the lumen of the graft. Organized thrombus may be the cause of graft thrombosis and eventual graft failure.

Repeated, direct punctures of the graft wall also require compression for hemostasis following the dialysis session. Excessive compression during hemostasis may cause decreased flow within the graft and thrombosis. Also, there is very little subcutaneous tissue between the surface of the skin and the graft wall reducing the capacity of extra luminal coagulation of the blood within the surrounding tissue and therefore causing reduced hemostasis at the end of the procedure.

What is needed is a dialysis access graft fistula that better provides for repeated cannulation while reducing the occurrence of ruptures of the graft, pseudoaneurysms, and the development of organized thrombus; and that reduces the problems discussed above with hemostasis.

SUMMARY OF THE INVENTION

The present invention meets the above-described needs by providing a graft that is particularly suitable for repeated dialysis. The graft provides a fistula between an artery and a vein and comprises a series of septums on both the arterial as well as the venous side. The septums are made of a stretchable material so that after puncture and withdrawal of the needle, the septum seals by itself. This avoids repeated puncture of the graft wall thereby prolonging the life of the graft. The development of the dialysis graft with puncture septums is a significant improvement over existing technology and can improve utilization by facilitating puncture and maintenance while reducing the risk of common complications such as pseudoaneurysms and thrombosis.

BRIEF DESCRIPTION OF THE DRAWINGS

The invention is illustrated in the drawings in which like reference characters designate the same or similar parts throughout the figures of which.

DESCRIPTION OF THE PREFERRED EMBODIMENTS

The present invention provides a dialysis graft with septums to provide improved access for dialysis, to reduce the uncertainty of puncture during the procedure, and furthermore, to protect the graft from damage caused by repeated punctures. In addition, this device will also eliminate the hemostasis factor discussed above.

Figure 1:
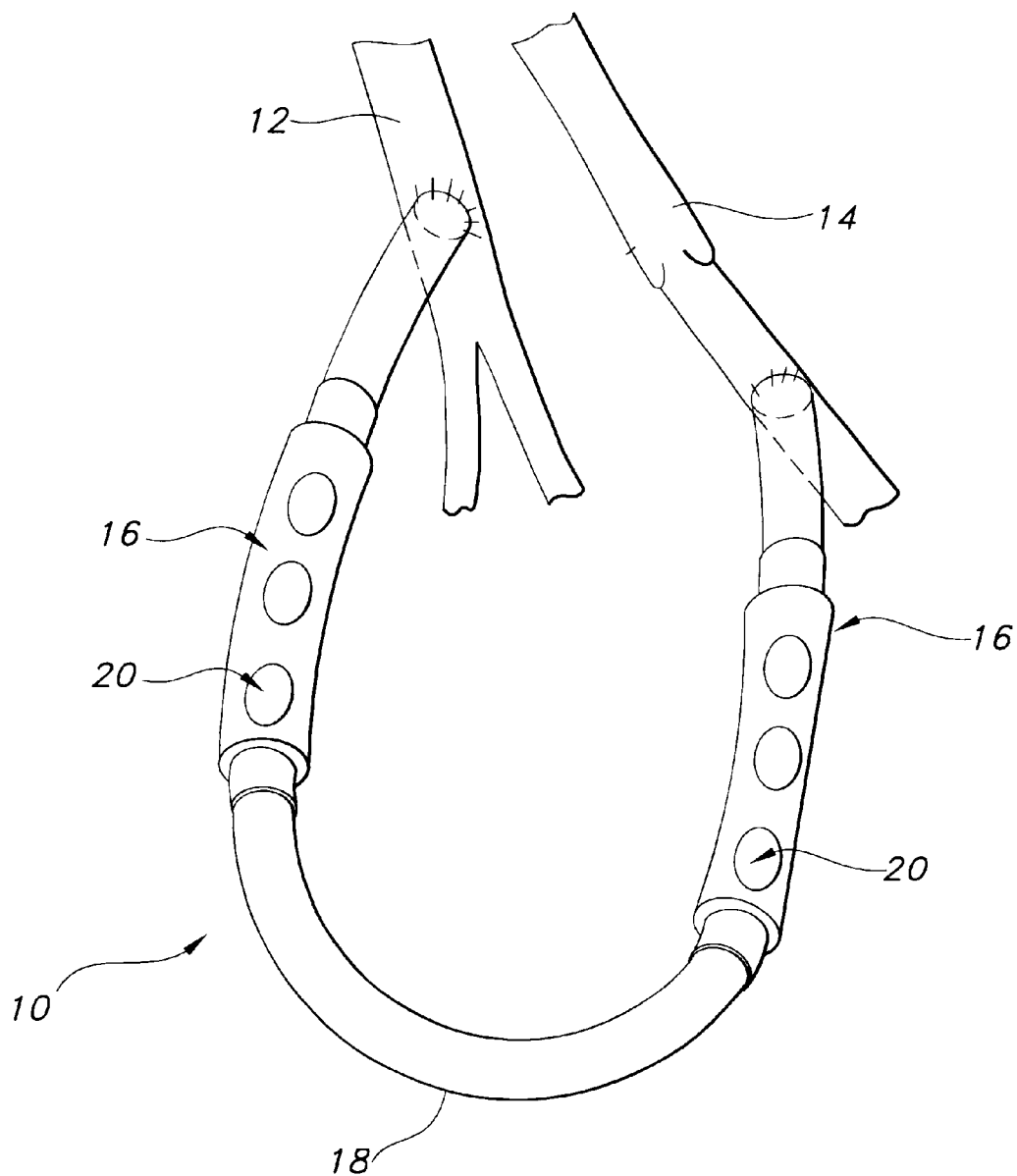
FIG. 1 is a perspective view of the dialysis graft.

As shown in FIG. 1, the dialysis graft 10 is anastomosed in end-to-side fashion between an artery 12 and a vein 14. The dialysis graft is composed of one, two, or more segments of plastic or metal chambers 16 on the arterial side and on the venous side. Regular graft segments 18 are connected to the artery 12 and the vein 14 and in between the chambers 16.

Figure 2:
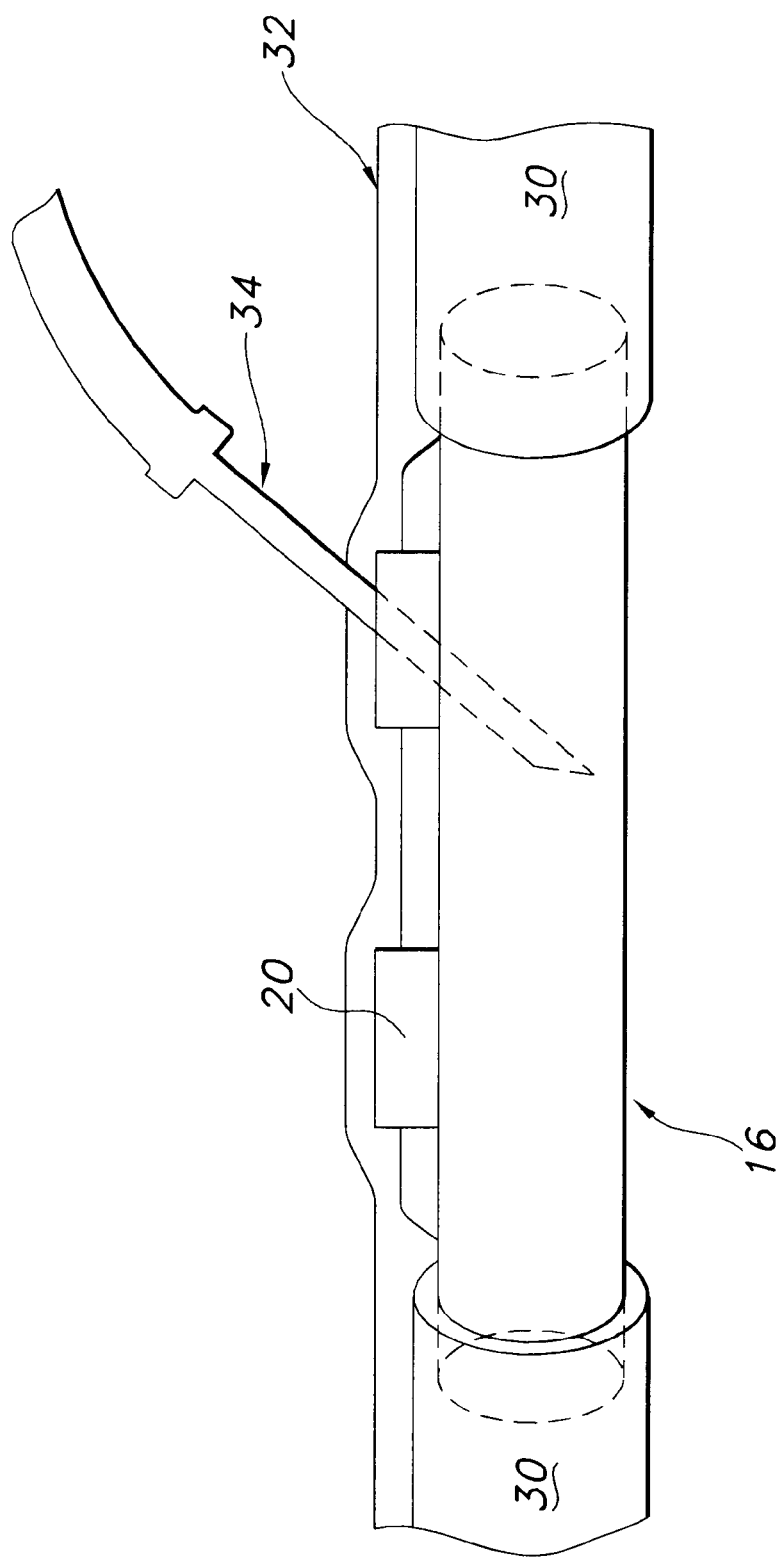
FIG. 2 is an enlarged side elevational view of the dialysis graft illustrating the positioning of the septums on the port chamber wall; and, FIG. 3 is an enlarged side elevational view of an alternate embodiment of the present invention.

A lateral view of a port chamber 16 is shown in FIG. 2. The port chamber 16 fits into the lumen 30 of a regular segment of the graft 18 by standard means. The port chamber 16 may be made of any suitable plastic material or metal. In the wall of the port chamber 16 are present a plurality of holes 17. Each hole 17 forms septum 20. Suitable materials for septums 20 include, but are not limited to, silicon and several other plastic polymers. Various materials for making septums 20 are well known to those skilled in the art. One port chamber 16 may contain several septums 20 distributed all around the port chamber 16. Since the graft 10 is typically placed close to the skin 32, the septums 20 are palpable underneath the skin for insertion of a needle 34. The external surface of the septum 20 is made of a stretchable material that is suitable for repeated punctures. One of the most commonly available materials is made of silicon. The septums 20 can be covered internally with Teflon or some other clot-resistant material.

The needle 34 used for puncturing the septum should be a coreless needle, i.e., it should not cut the seal of the septum 20 but should open a hole that may tightly close after needle 34 withdrawal. One example of a suitable needle 34 for puncturing the septum 20 is a needle 34 with a beveled end. The beveled end will puncture the septum 20 but will not remove a core from the septum 20 material which is then able to self-seal after removal of the needle 34. Each septum 20 should withstand several punctures and not suffer significant wear and tear.

A minimum of two septums 20 should be available on the arterial and venous side of graft 10 to allow healing of adjacent skin and to increase the number of allowable punctures. For example, for a patient requiring dialysis three times a week, a suitable dialysis graft 10 should have provision for 156 punctures per year. If there are two septums 20 on each side, each septum 20 will be punctured 78 times a year. A preferable dialysis graft 10 should be able to be used for several years.

Figure 3:
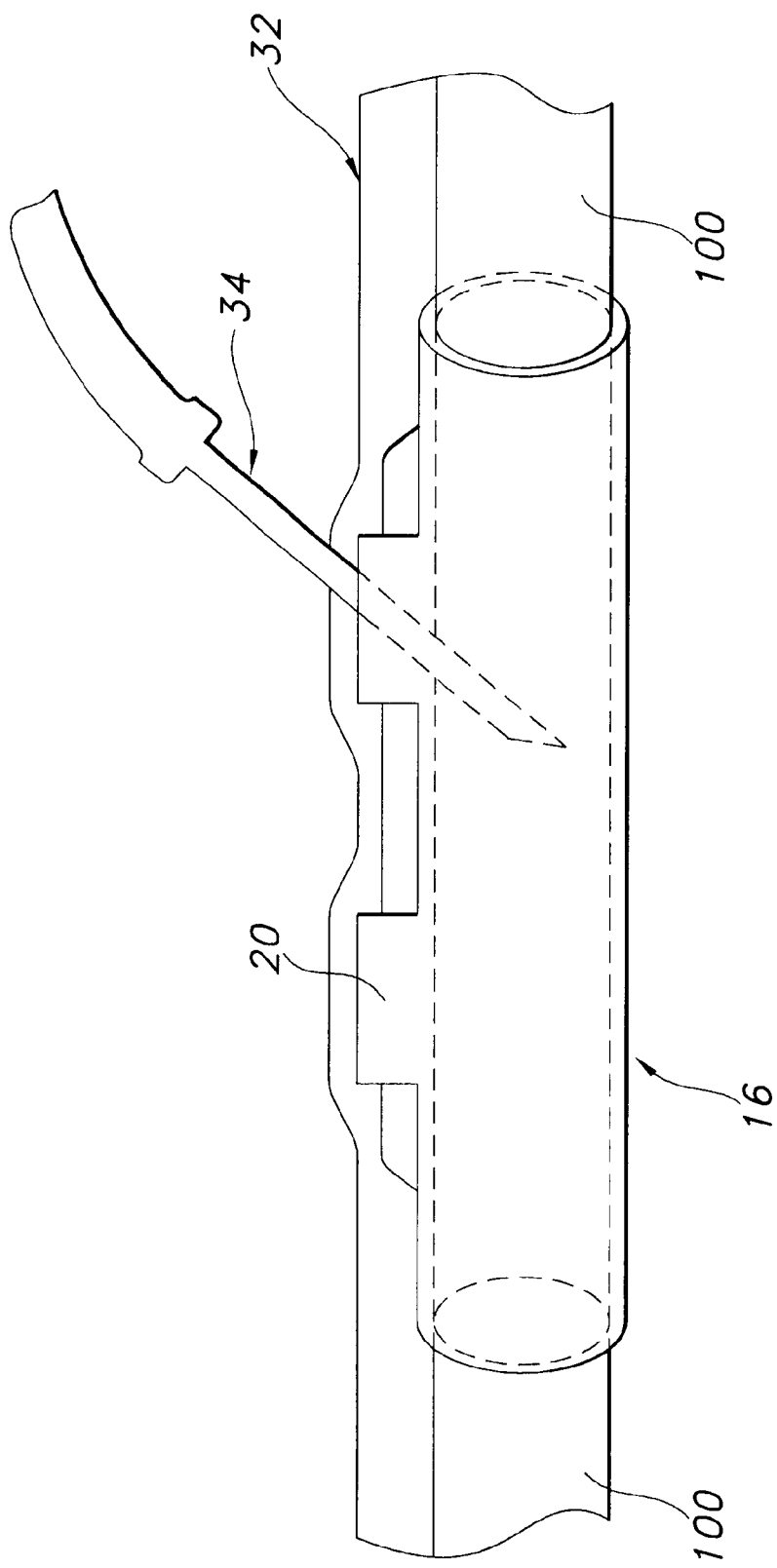

In an alternate embodiment, in FIG. 3, a graft 100 is disposed through the inside of a tubular port chamber 16 of the present invention. Instead of connecting the graft 100 to opposite ends of the chamber 16, the graft 100 extends completely through the inside of the port chamber 16.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. An implantable dialysis graft, comprising:
  a tubular graft of biocompatible material for conducting fluid and extending between an artery and a vein, and,
  at least two tubular port chambers in fluid communication with the tubular graft, the port chamber having at least one septum defined therein, the septum formed by a hole defined in the port chamber, the hole being covered by a biocompatible self-resealing, penetrable material;
  wherein the dialysis graft is entirely subcutaneous and is capable of being cannulated by a needle disposed through the port chamber to achieve an effective flow rate for dialysis.

2. The vascular device of claim 1, wherein the at least one tubular port chamber is spliced into the graft.

3. The vascular device of claim 1, wherein the tubular port chamber is attached to the graft at opposite ends such that a substantially continuous lumen is formed.

4. The vascular device of claim 1, wherein the at least one tubular port chamber comprises a first port chamber disposed on an arterial side of the graft and a second port chamber disposed on a venous side of the graft.

5. The vascular device of claim 1, wherein the tubular port chamber is disposed substantially in axial alignment with the tubular graft.

6. The vascular device of claim 1, wherein the at least one septum on the tubular port chamber has sidewalls that extend beyond the graft such that the septum is palpable underneath the skin after the device has been implanted.

7. The vascular device of claim 1, wherein the tubular graft is anastomosed in end-to-side fashion to an artery at one end and is anastomosed in end-to side fashion to a vein at an opposite end.

8. The vascular device of claim 1, wherein the plurality of septums are disposed along a longitudinal axis of the port chamber.

9. The vascular device of claim 1, wherein the graft is shaped in the form of a loop.

10. The vascular device of claim 1, wherein the graft is straight.

11. An implantable dialysis graft for connecting an artery to a vein, the device comprising:
  at least two tubular port chambers having at least one septum defined therein, the septum formed by a hole defined in the port chamber, the hole being covered by a biocompatible, self-resealing, penetrable material;
  a tubular graft extending between an artery and a vein and disposed through the inside of the port chambers such that access to the graft is available through at least one septum; and,
  wherein the dialysis graft is entirely subcutaneous and is capable of being cannulated by a needle disposed through the port chamber to achieve an effective flow rate for dialysis.

12. An implantable dialysis graft for connecting an artery to a vein, the device comprising:
  a) a tubular graft of biocompatible material for conducting fluid, the tubular graft anastamosed to the artery at a first end and anastomosed to the vein at a second end;
  b) a tubular, biocompatible, arterial-side port chamber that is in fluid communication with the graft, the port chamber having at least one septum defined therein, the septum formed by a hole defined in the port chamber, the hole being covered by a biocompatible, self-resealing, penetrable material; and,
  c) a tubular, biocompatible, venous-side port chamber that is in fluid communication with the graft, the port chamber having at least one septum defined therein, the septum formed by a hole defined in the port chamber, the hole being covered by a biocompatible, self-resealing, penetrable material;
  d) wherein the prosthetic device is entirely subcutaneous and is capable of being cannulated by a needle disposed through the port chamber to achieve a flow rate of about 150 to 400 ml of blood/minute.

13. The vascular device of claim 12, wherein the at least one arterial-side tubular port chamber is connected at opposite ends to the graft such that a continuous lumen is formed.

14. The vascular device of claim 12, wherein the at least one venous-side tubular port chamber is connected at opposite ends to the graft such that a continuous lumen is formed.

15. The vascular device of claim 12, wherein the at least one arterial-side tubular port chamber is disposed in axial alignment with the tubular graft.

16. The vascular device of claim 12, wherein the at least one venous-side tubular port chamber is disposed in axial alignment with the tubular graft.

17. The vascular device of claim 12, wherein the at least one septum on the at least one arterial-side tubular port chamber and on the at least one venous-side tubular port chamber have sidewalls that extend beyond the graft such that the septum is visible underneath the skin after the device has been implanted.

18. The implantable dialysis graft of claim 12, wherein the at least one septum is disposed along a longitudinal axis of the septum.

19. The vascular device of claim 12, wherein the graft is shaped in the form of a loop.

20. The vascular device of claim 12, wherein the graft is straight.

21. An implantable dialysis graft for forming a fistula for cannulation, comprising:

means for conducting the flow of blood from an artery to a vein to form the fistula;

means for cannulating the fistula, the cannulating means comprising at least two tubular port chambers in fluid communication with the tubular graft, the port chamber having at least one septum defined therein, the septum formed by a hole defined in the port chamber, the hole being covered by a biocompatible self-resealing, penetrable material; and, wherein the prosthetic device is entirely subcutaneous and is capable of being cannulated by a needle disposed through the port chamber to achieve an effective flow rate for dialysis.

22. The vascular device of claim 21, wherein the cannulating means further comprises a first cannulating means disposed on an arterial side of the conducting means and a second cannulating means disposed on a venous side of the conducting means.

* * * * *